United States Patent [19]

Ashby et al.

[11] 4,358,962
[45] Nov. 16, 1982

[54] SCORE LINE FOLDING TESTER

[75] Inventors: C. William Ashby, Naperville; Stephen A. Morse, Downers Grove, both of Ill.

[73] Assignee: Container Corporation of America, Chicago, Ill.

[21] Appl. No.: 257,536

[22] Filed: Apr. 27, 1981

[51] Int. Cl.³ .............................................. G01N 3/20
[52] U.S. Cl. ................................................... 73/849
[58] Field of Search ................ 73/849, 850, 851, 854, 73/862.45, 862.46, 862.47, 862.48

[56] References Cited

U.S. PATENT DOCUMENTS 2,442,713  6/1948  Shartle ................................. 73/849

FOREIGN PATENT DOCUMENTS 833510  4/1960  United Kingdom ................. 73/849

Primary Examiner—Jerry W. Myracle
Attorney, Agent, or Firm—Richard W. Carpenter; Davis Chin

[57] ABSTRACT

An apparatus for measuring the force required to fold a paperboard about a score line comprises a force applying arm and a device for measuring a torque related to the force necessary to cause folding of the paperboard at the score line.

3 Claims, 3 Drawing Figures

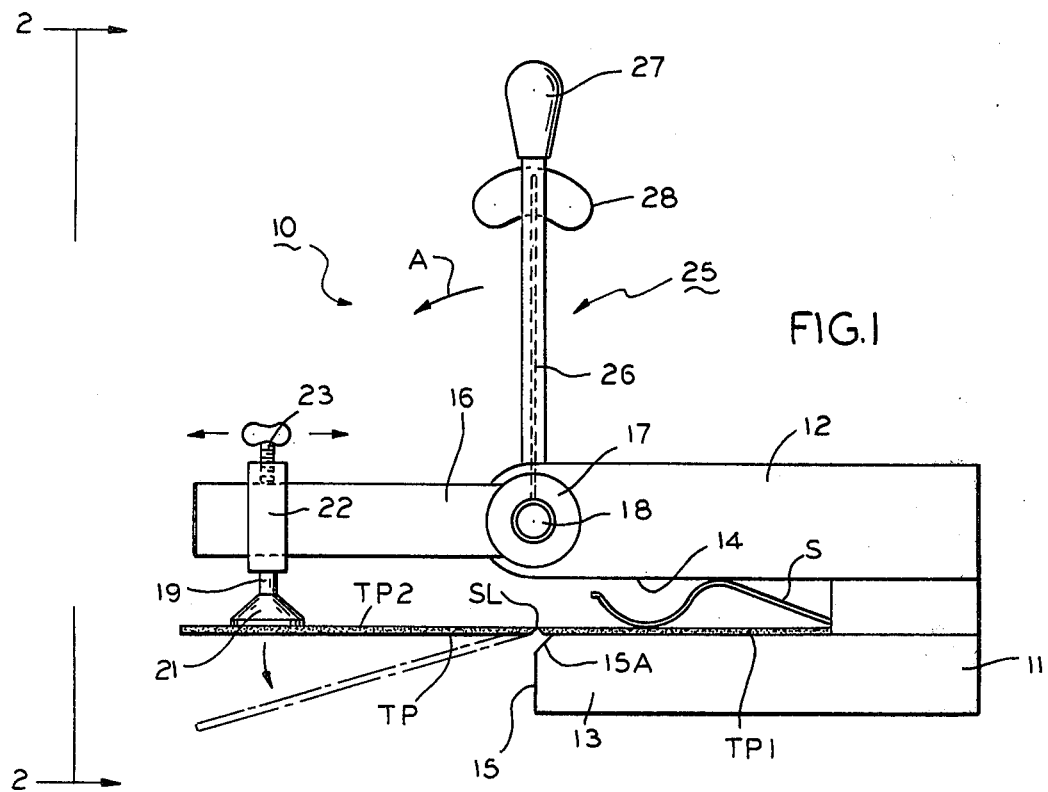
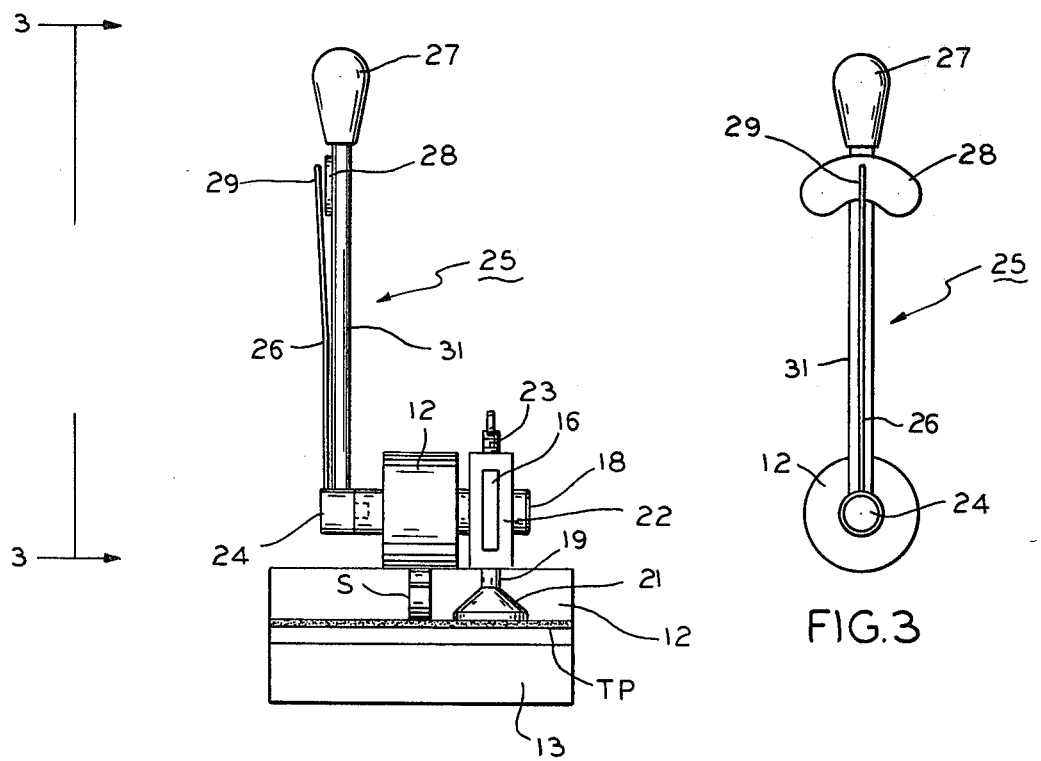

SCORE LINE FOLDING TESTER

BACKGROUND OF THE INVENTION

This invention relates generally to apparatus for testing paperboard and more particularly, to an apparatus for measuring the force required to fold a paperboard about a score line.

SUMMARY OF THE INVENTION

The disclosed structure finds special application in the fabrication of paperboard containers where it is desirable to ascertain the force necessary to achieve folding about score lines formed in the paperboard. The amount of resistance to folding is desired to be known especially with respect to container forming machines and case loading machines.

The invention structure makes it possible to ascertain the rigidity of a fold line, and the degree of scoring necessary, to the end that the folding force necessary may be brought within proper limits.

BRIEF DESCRIPTION OF THE DRAWINGS

The objects and advantages of the present invention will become more fully apparent from the following detailed description when read in conjunction with the accompanying drawings wherein:

FIG. 1 is a front elevational view showing the folding tester according to the present invention;

FIG. 2 is a side elevation view looking in the direction of the arrows 2—2 of FIG. 1; and FIG. 3 is an enlarged view of the scale and dial indicator shown in FIG. 1.

DESCRIPTION OF THE PREFERRED EMBODIMENT

Referring now in detail to the various views of the drawings, a folding tester is denoted generally by the reference numeral 10 and includes a fixture 11 for holding a test piece TP in position therein. Test piece TP has a score line SL, and it is desired to determine the resistance to folding thereof.

Fixture 11 has a lower limb 13 and an upper limb 12, these being spaced apart to define a slot 14 therebetween into which the test piece TP is introduced. Test piece TP is divided by the score line SL into a test piece portion TP, entrant to the slot 14, and a portion TP$_2$ extending out of slot 14.

The score line SL lies on an axis parallel to a front edge 15 of lower limb 13, and an edge 15 is chamfered at 15A to enable portion TP$_2$ to flex with respect to portion TP$_1$ retained in slot 14. An undulating leaf spring S is interposed between the test piece portion TP$_1$ and the upper limb 12 to hold the test piece portion TP$_1$ in position in the slot 14.

A force applying arm 16 is connected pivotally to a hub 17 which is fixed to a shaft 18 journaled in upper limb 12, and the center of the shaft 18 lies in a vertical plane including the axis of the score line SL. Force applying means 19 is supported on the force applying arm 16, and the lower end of the force applying means 19 terminates in a force applying foot 21 bearing against test piece portion TP$_2$. The force applying means 19 is adjustable horizontally to the desired position along the force applying arm 16 by a slide bracket 22 supporting the means 19, and the bracket 22 may be locked in position by a thumb screw 23 tapped into bracket 22.

Structure is provided for measuring the torque as a function of the force necessary to flex or bend portion TP$_2$ about the score line SL. To this end, a torque measuring devicd 25 is mounted rotatably on the shaft 18 and is made fast therewith. Device 25 has a hub 24 having extending therefrom a flex arm 26, the upper end of flex are 26 terminating in an actuating handle 27. An indicating dial scale 28 is mounted on the flex arm 26, and the scale 28 cooperates with a dial indicator 29 mounted at the upper end of an arm 31 attached rigidly to the hub 24.

When the test piece TP is placed in position on the fixture 11, the force applying means 19 and foot 21 are placed in proper position on portion TP$_2$. When the handle 27 of the torque measuring device 25 is rotated in a counter-clockwise direction along arrow A as best seen in FIG. 1, the portion TP$_2$ will be folded about the score line SL with respect to portion TP$_1$ to move to the dotted line position seen in FIG. 1.

The dial indicator 29 will move with respect to the dial scale 28 as the arm 26 is flexed to give a value related to the torque at shaft 18 and the pressure at force applying means 19, all as a measure of the force required to bend the test piece TP at the score line SL.

While there has been illustrated and described what is at present to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out this invention, but that the invention will include all embodiments falling within the scope of the appended claims.

What is claimed is:

1. An apparatus for measuring the force necessary for the folding of paperboard about a score line therein comprising:
   (a) a fixture for holding a paperboard test piece having a score line thereon;
   (b) said fixture having upper and lower spaced apart limbs defining a slot therebetween for entrance thereinto of a portion of said test piece;
   (c) the score line of said test piece lying along an axis coincident with an edge of said lower limb at the entrance to said slot;
   (d) a force applying arm pivoted to said upper limb and having force applying means supported thereby in contact with that portion of the test piece extending beyond said slot;
   (e) means for measuring a torque related to the force necessary to cause folding of the test piece at said score line; and
   (f) said measuring means being mounted upon a shaft fixed to said force applying arm and rotatable with respect to said upper spaced apart limb.

2. An apparatus as claimed in claim 1, wherein a spring is interposed between said test piece and said upper limb for holding said test piece in position in said slot.

3. An apparatus as claimed in claim 1, wherein said measuring means includes an indicating dial scale mounted on an arm extending from said shaft, and a dial indicator mounted on a force applying arm which is displaced upon force being applied by the force applying arm.

* * * * *